United States Patent [19]
Wang

[11] Patent Number: 5,421,822
[45] Date of Patent: Jun. 6, 1995

[54] REHABILITATING APPARATUS FOR AN INJURED LEG

[76] Inventor: Tzu-Chiang Wang, 9600 Bellaire, Suite 232, Houston, Tex. 77036

[21] Appl. No.: 134,301

[22] Filed: Oct. 8, 1993

[51] Int. Cl.⁶ ............................................. A61F 5/00
[52] U.S. Cl. ...................................................... 602/27
[58] Field of Search .................. 602/5, 12, 23, 27, 28, 602/29, 30

[56] References Cited
U.S. PATENT DOCUMENTS

| | | | |
|---|---|---|---|
| 4,964,402 | 10/1990 | Grim et al. | 602/27 X |
| 5,088,480 | 2/1992 | Wang | 602/27 |
| 5,282,483 | 2/1994 | Wang | 602/27 X |

FOREIGN PATENT DOCUMENTS 2168610  6/1986  United Kingdom ................ 602/28

Primary Examiner—Richard J. Apley
Assistant Examiner—Beverly A. Meindl
Attorney, Agent, or Firm—Ladas & Parry

[57] ABSTRACT

The rehabilitating apparatus includes an elongated rigid main support plate conforming to a leg and having a first engaging unit at a bottom end thereof, a rigid foot support plate having a second engaging unit at a rear end and a plurality of fastening straps. The first engaging unit of the main support plate engages detachably the second engaging unit of the foot support plate to define an L-shaped member.

6 Claims, 7 Drawing Sheets

5,421,822

REHABILITATING APPARATUS FOR AN INJURED LEG

BACKGROUND OF THE INVENTION

1. Field of the Invention

The invention relates to a rehabilitating apparatus, more particularly to a rehabilitating apparatus for an injured leg.

2. Description of the Related Art

A conventional rehabilitating apparatus for an injured leg includes an L-shaped rigid plate which conforms substantially to the injured leg for receiving the same and which has two opposite faces and two opposite longitudinal peripheral edges; means for limiting lateral movement transverse to and between the longitudinal peripheral edges of the L-shaped rigid plate, thereby confining the injured leg to a predetermined position on one of the opposite faces; and means for securing the injured leg to the L-shaped rigid plate.

A main drawback of the conventional apparatus for rehabilitating an injured leg is that the L-shaped rigid plate is cumbersome and cannot be folded in order to minimize the size thereof so as to facilitate packaging, storage and transport of the same.

SUMMARY OF THE INVENTION

A main objective of the present invention is to provide a rehabilitating apparatus for an injured leg which can be disassembled into pieces so as to minimize its size, thereby facilitating packaging, storage and transport of the same.

A second objective of the present invention is to provide an apparatus which is constituted by a rigid main support plate and a rigid foot support plate which is attached detachably to the main support plate so as to form an L-shaped member.

A third objective of the present invention is to provide a rehabilitating apparatus which is adjustable so that it can be employed to any injured leg so as to rehabilitate the latter regardless of the width and the length of the leg.

Accordingly, the rehabilitating apparatus for an injured leg includes an elongated rigid main support plate for supporting a calf of the leg, the main support plate having a top end, a bottom end, two opposed faces and a first engaging unit formed at the bottom end; an elongated auxiliary cushioning plate; means for fastening the auxiliary cushioning plate detachably and removably to the top end of the main support plate and for permitting the auxiliary cushioning plate to extend beyond the top end of the main support plate along a longitudinal direction of the latter to vary a combined length of the main support plate and the auxiliary cushioning plate; a rigid foot support plate conforming substantially to a foot and having a first end and a second end with a second engaging unit which is engageable detachably with the first engaging unit of the main support plate to connect the foot support plate and the main support plate to form an L-shaped member; and means for securing the foot and the calf when the injured leg is provided on the L-shaped member.

In the given preferred embodiments, male-and-female connection elements are used for the first and second engaging units so that they can be disassembled when the apparatus is not in use. The fastening means for connecting the rigid main support plate and the auxiliary cushioning plate can be a plurality of Velcro straps or a row of aligned holes formed at the top end of the main support plate and lying along a longitudinal length of the main support plate, a plurality of aligned slots formed adjacent to a lower end of the auxiliary cushioning plate and lying along a longitudinal length of the auxiliary cushioning plate, and a plurality screw fasteners. The securing means for securing the calf and the foot can be any suitable fastening strap so long as it can immobilize the injured leg after the latter is provided on the L-shaped member.

When not in use, the L-shaped member of the rehabilitating apparatus can be disassembled, thereby minimizing its size to facilitate packaging, storage and transport of the same.

BRIEF DESCRIPTION OF THE DRAWINGS

Other features and advantages of the present invention will become apparent in the following detailed description of the preferred embodiment with reference to the accompanying drawings, in which.

DETAILED DESCRIPTION OF THE PREFERRED EMBODIMENTS

Figure 1:
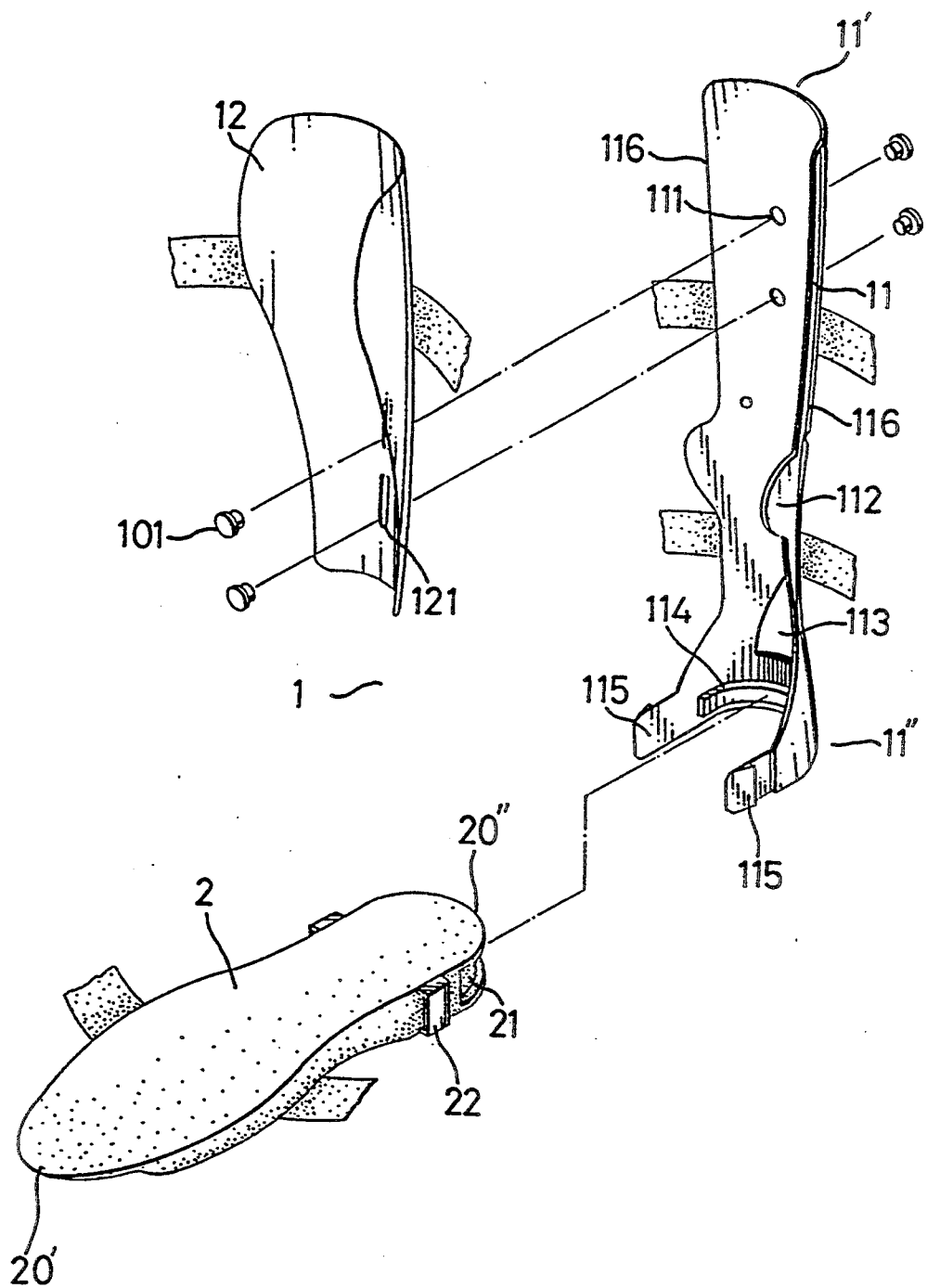
FIG. 1 is an exploded view of a first preferred embodiment of a rehabilitating apparatus for an injured leg according to the present invention.

Before the present invention is described in greater detail, it should be noted that similar reference numerals are used to denote similar elements throughout the specification.

Figure 2:
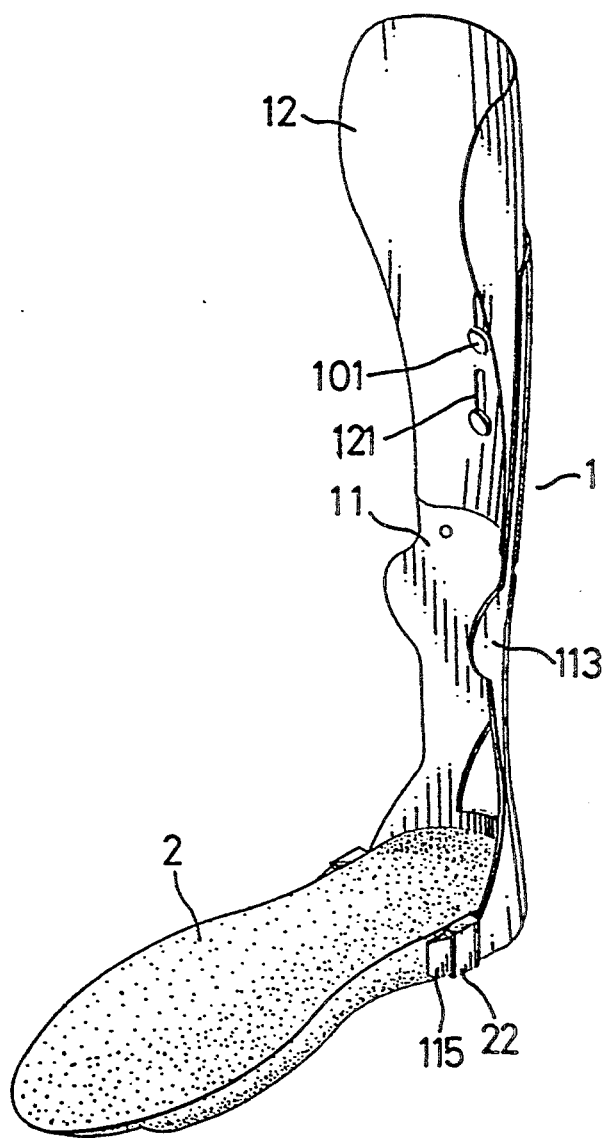
FIG. 2 is an assembled view of the first preferred embodiment.

Referring to FIGS. 1 and 2, an exploded view of a first preferred embodiment of a rehabilitating apparatus 1 for an injured leg is shown to comprise an elongated rigid main support plate 11, an auxiliary cushioning plate 12, means for fastening the auxiliary cushioning plate 12 detachably and removably to a top end of the main support plate 11 and for permitting the cushioning plate 12 to extend beyond the top end of the main support plate 11 to vary a combined length of the main support plate 11 and the auxiliary cushioning plate 12, a rigid foot support plate 2, and means for securing the injured leg after the latter is placed on the apparatus 1 of the present invention.

Note that the securing means used in all of the preferred embodiments can be any suitable securing article, such as conventional bandages or Velcro straps.

The rigid main support plate 11 conforms substantially to a calf of the leg and has a top end 11', a bottom end 11''', two opposite faces, two opposed longitudinal peripheral edges 116 with a pair of preventing tabs 112, a first engaging unit formed at the bottom end 11''', and an opening 113 adjacent to the first engaging unit. The purpose of the opening 113 will be described in the succeeding paragraphs. The first engaging unit includes a curved piece formed at the bottom end of the main support plate 11. The curved piece has two opposed ends, an internal face, an external face and a pair of plug members 115 extending respectively from the opposed ends of the curved piece. A curved insert piece 114 is formed integrally on the internal face of the curved piece of the main support plate 11. The preventing tabs 112 limit a lateral movement of the injured leg so as to confine the same on the internal face of the main support plate 11 between the two longitudinal peripheral edges 16.

The fastening means employed in the first preferred embodiment includes two aligned holes 111 formed along a longitudinal direction of the main support plate 11 adjacent to the top end 11' of the latter, two aligned slots 121 formed along a longitudinal direction of the auxiliary cushioning plate 12 adjacent to a lower end of the same, and two screw fasteners 101 which extend through the aligned holes and slots 111, 121 in order to fasten adjustably the auxiliary cushioning plate 12 to the main support plate 11. When the auxiliary cushioning plate 12 is attached adjustably to the main support plate 11, a portion of the cushioning plate 12 extends beyond the top end 11' of the main support plate 11.

The rigid foot support plate 2 conforms substantially to a foot and has a front end 20' and a rear end 20'' with a second engaging unit. The second engaging unit includes a recess 21 formed at the rear end 20'' and two socket members 22 which are located on two sides of the recess 21 to receive engageably the plug members 115 when the curved insert piece 114 of the main support plate 11 is inserted into the recess 21 of the foot support plate 2 so as to form an L-shaped member, as shown in FIG. 2.

Figure 3:
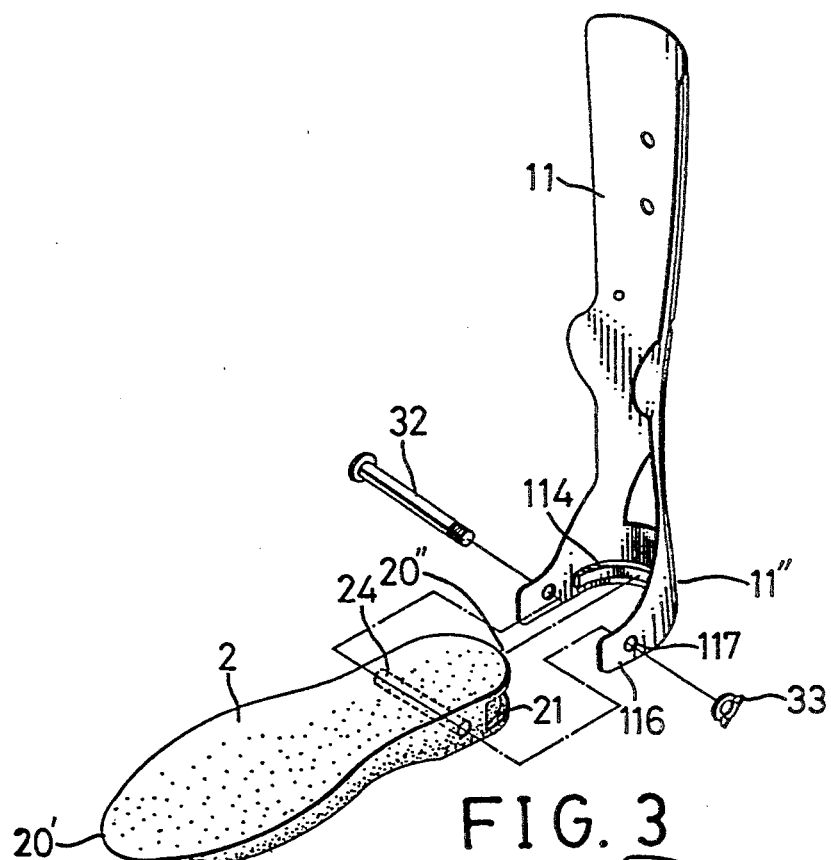
FIG. 3 is an exploded view of a second preferred embodiment of a rehabilitating apparatus for an injured leg according to the present invention.

Referring to FIG. 3, a second preferred embodiment of a rehabilitating apparatus comprises a rigid main support plate 11 with a first engaging unit that includes a curved piece with two opposed connecting stubs 116, an internal face, an external face and a curved insert piece 114 that is formed integrally on the internal face of the curved piece. Each of the connecting stubs 116 is provided with a mounting hole 117. The second engaging unit of the rigid foot support plate 2 includes a recess 21 that is formed at the rear end 20'' of the foot support plate 2 and a through-hole 24 that is formed transverse to a longitudinal length of the foot support plate 2 and that is located adjacent to the recess 21. When the curved insert piece 114 of the main support plate 11 is inserted into the recess 21 of the foot support plate 2, the mounting holes 117 of the connecting stubs 116 are aligned with the through-hole 24 of the foot support plate 2 so as to permit fastening of the foot support plate 2 by means of a screw fastener that includes a locking bolt and nut 32, 33.

Figure 4:
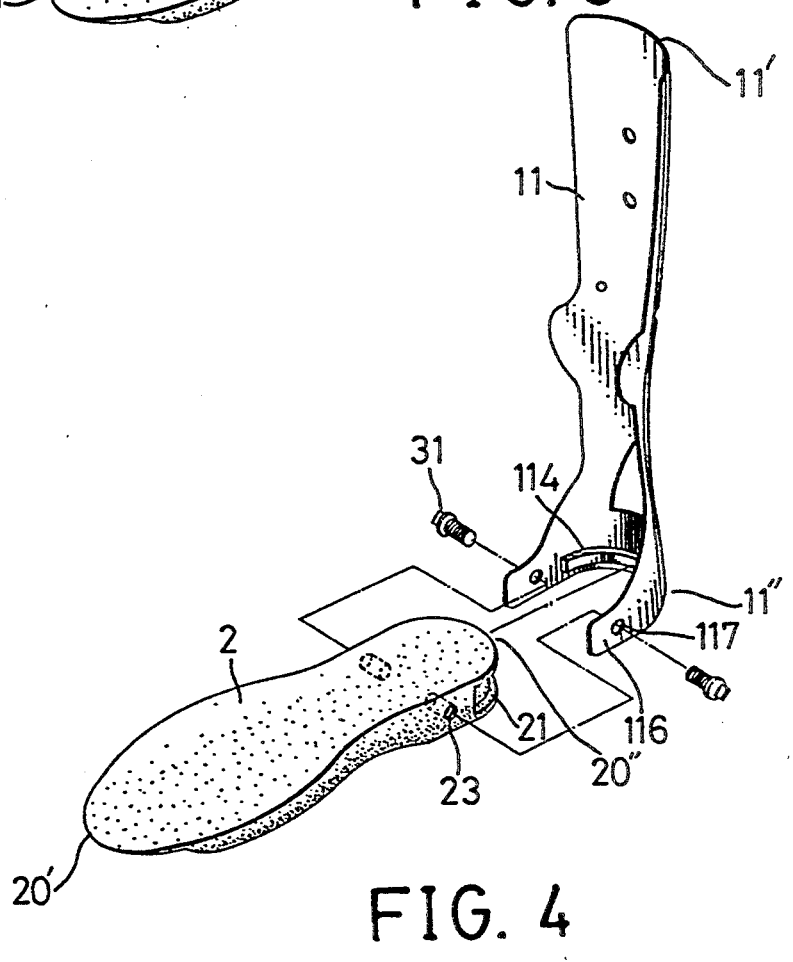
FIG. 4 is an exploded view of a third preferred embodiment of a rehabilitating apparatus for an injured leg according to the present invention.

Referring to FIG. 4, in a third preferred embodiment of the rehabilitating apparatus of the present invention, the engaging units are the same as those of the second preferred embodiment except that the second engaging unit has two opposed threaded blind bores 23 and a pair of screw fasteners, such as locking bolts 31, which can be threaded in the blind bores 23 via the mounting holes 117 of the connecting stubs 116 after the insert piece 114 of the main support plate 11 is inserted into the recess 21 at the rear end 20'' of the foot support plate 2.

Figure 5:
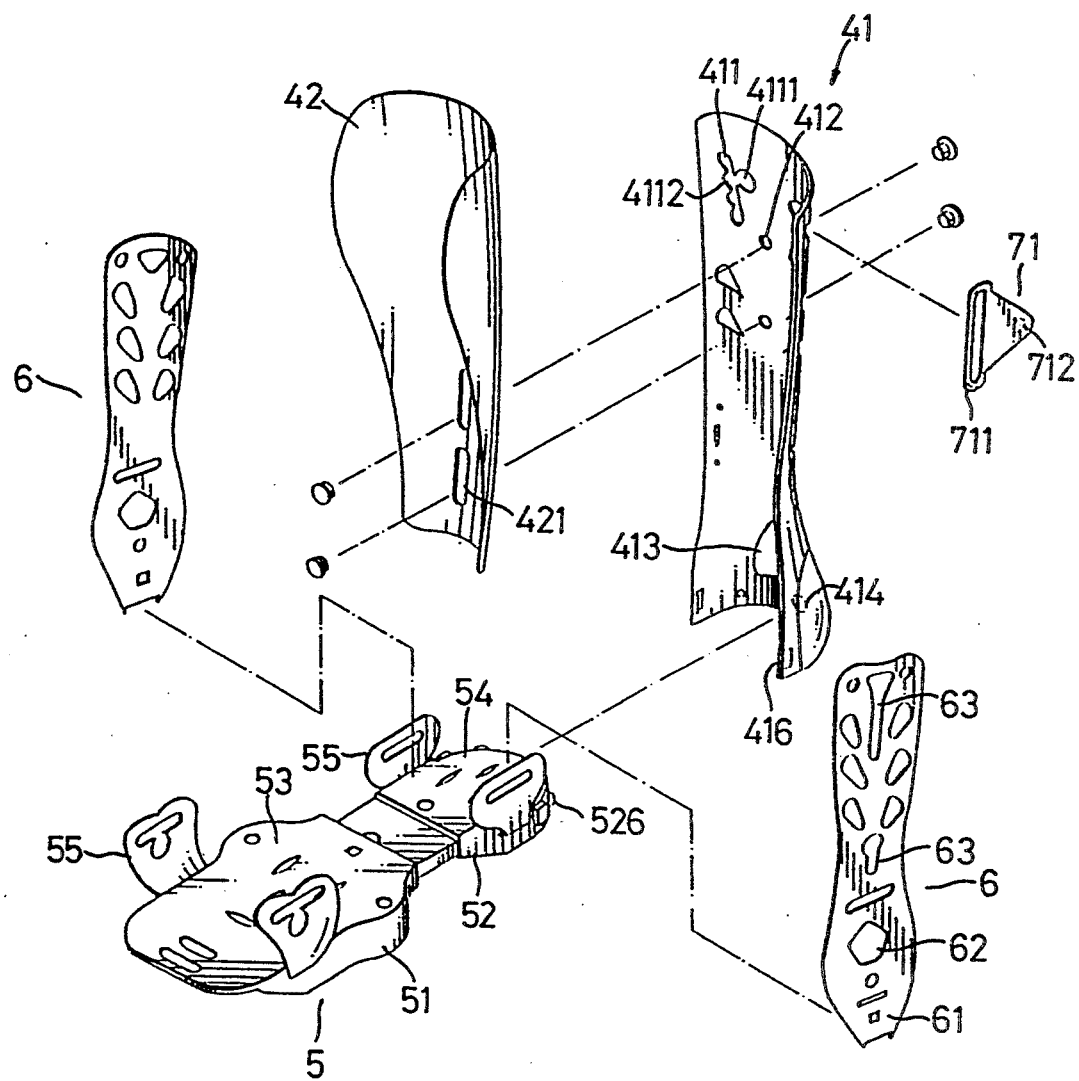
FIG. 5 is an exploded view of a fourth preferred embodiment of a rehabilitating apparatus for an injured leg according to the present invention.
Figure 6:
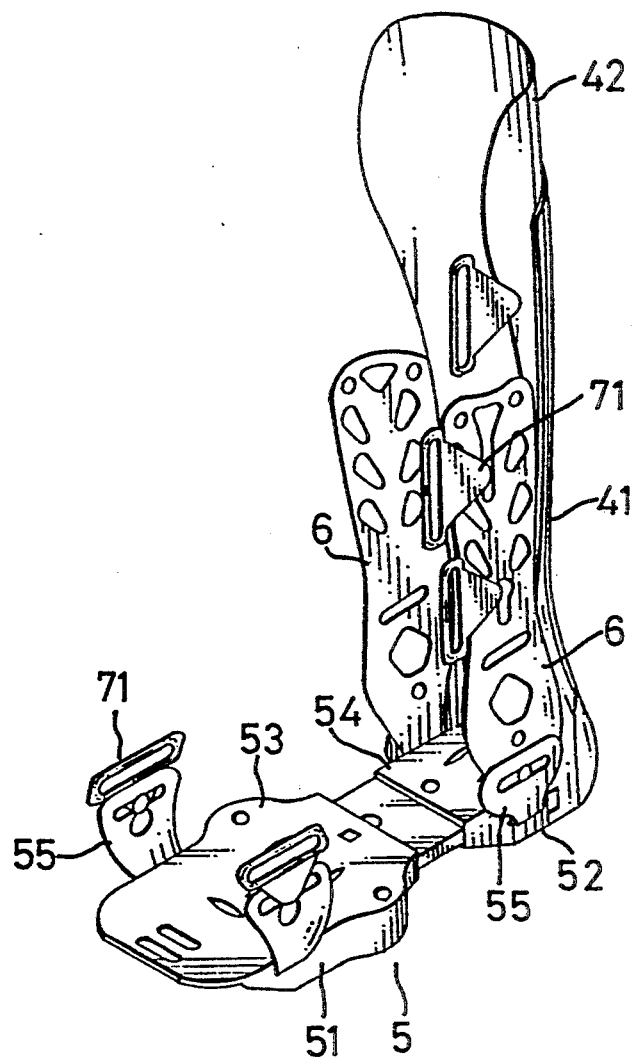
FIG. 6 is an assembled view of the fourth preferred embodiment.

Referring to FIGS. 5 and 6, a fourth preferred embodiment of the apparatus is shown to be generally similar to the previous embodiments with exception that the main support plate 41 has two opposite mounting holes 411 adjacent to the top end thereof. Each of the mounting holes 411 is formed with an elongated slot 4112 and a circular opening 4111 which is communicated with the elongated slot 4112. A fastening member 71 has an engaging ring 711 and a positioning member 712 with an enlarged head (not shown) and a neck portion (not shown) which extends movably in the slot 4112 after the enlarged head extends through the circular opening 4111, thereby permitting a Velcro strap to pass through the engaging ring 711. The first and second engaging units of this embodiment are male-and-female connection means that include resilient projections 414, 526 and recesses 416, 524 (shown in FIG. 7) formed respectively on the main support plate 11 and the foot support plate 5.

Figure 7:
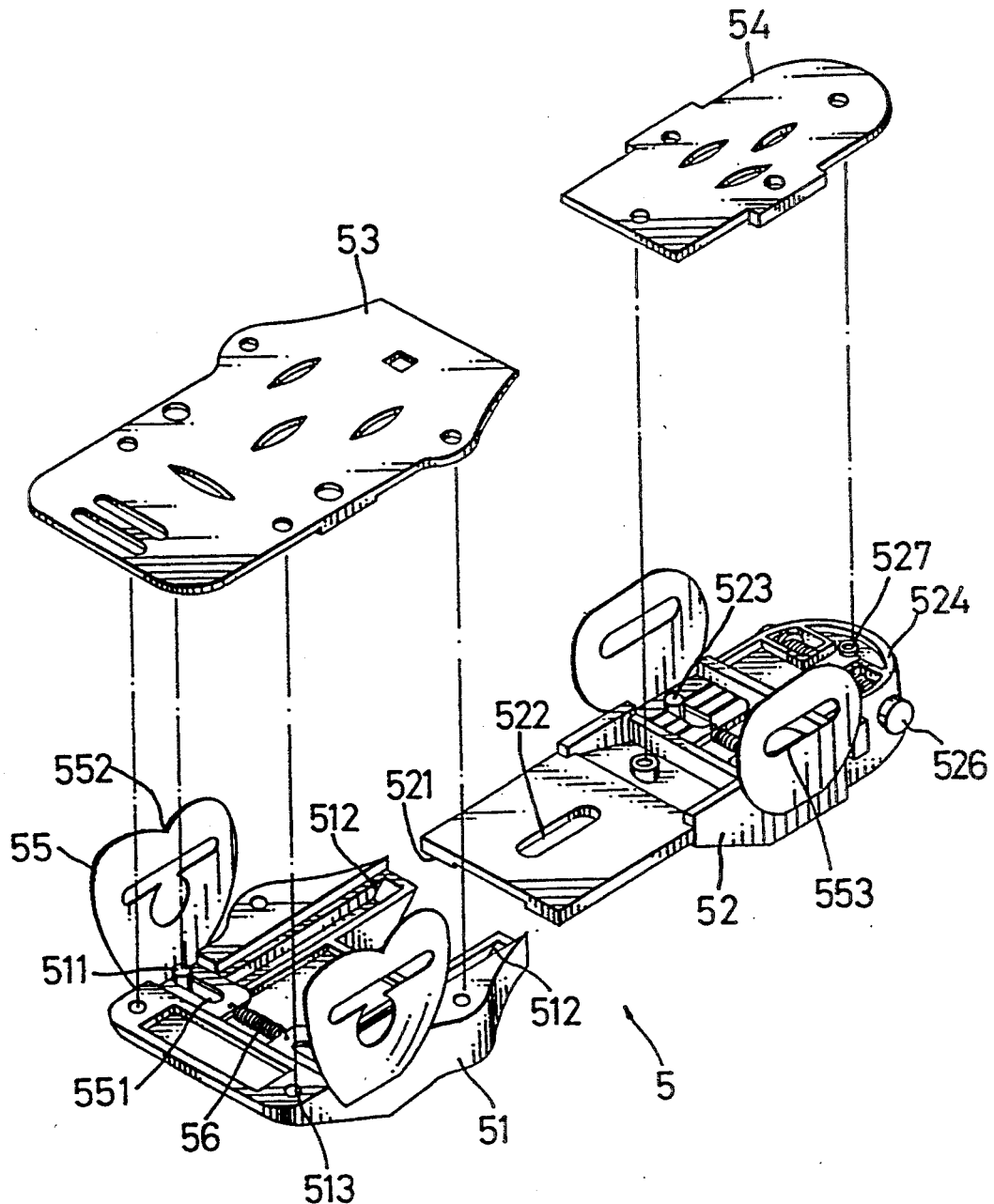
FIG. 7 is an exploded view of a rigid foot support plate employed in the fourth preferred embodiment.
Figure 8:
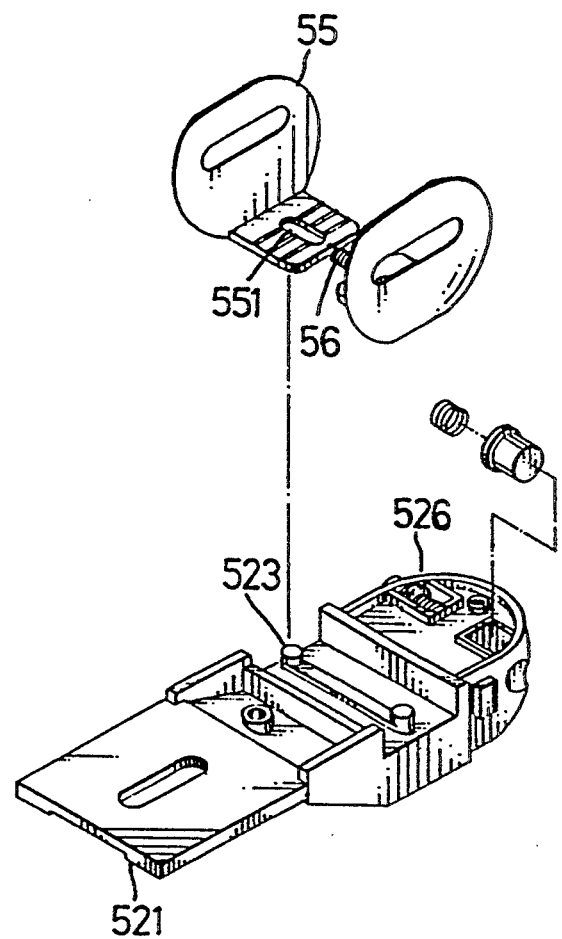
FIG. 8 shows an enlarged view of a second section of the rigid foot support plate shown in FIG. 7.

Referring to FIGS. 7 and 8, the rigid foot support plate 5 is constituted by a first section 51, a second section 52 and two cover members 53, 54 to cover respectively the first and second sections 51, 52. The first section 51 has an elongated groove 512 and four threaded holes 513, while the second section 52 has a longitudinal protrusion 521 with two threaded holes 527. The longitudinal protrusion 521 is received slidably in the elongated groove 512. Each of the first and second sections 51, 52 has two opposed vertical positioning rods 511, 1523 formed along two opposite longitudinal peripheral edges and two L-shaped connecting members 55 disposed on each of the sections 51, 52. Each of the L-shaped connecting members 55 has a first part which contacts a respective one of the first and second sections 51, 52 and a second part which extends substantially perpendicular from the first part. The first part of the L-shaped connecting member 55 has an elongated first slot 551 which extends transverse to a longitudinal length of the foot support plate 5 and which permits the vertical positioning rod 511 to pass through the same, thereby preventing the L-shaped connecting members 55 from disengaging the respective sections 51, 52. The second part of each L-shaped member 55 has an elongated second slot 552 which extends parallel to the longitudinal length of the foot support plate 5. The L-shaped connecting members 55 are resiliently connected to one another by means of a tension spring 56. The cover members 53, 54 are respectively threaded on the first and second sections 51, 52 of the foot support plate 5 after adjusting the longitudinal length of the same. The second section 52 of the foot support plate 5 is further provided with two fastening straps 6 which are respectively connected to the L-shaped connecting members 55. Since each fastening strap 6 has a plurality of mounting holes, two fastening members 71 are attached detachably thereto to facilitate passage of a Velcro strap (not shown) when immobilizing an injured leg. Under such a condition, the L-shaped connecting members 55 expand resiliently and outwardly outward of the foot support plate 5 in order to receive portions of a foot which has a width that is larger than that of the foot support plate 5.

The first and second sections 51, 52 can be further provided with a stack at a bottom portion to facilitate walking purposes. After the injured leg is immobilized on the rehabilitating apparatus with the use of fastening means, such as Velcro straps, the opening 413 adjacent to a bottom end of the main support plate 41 permits a heel of the injured leg to protrude therefrom to facilitate the recuperating process. The auxiliary cushioning plate 42 in the preferred embodiment can be attached adjustably to the main support plate 41 in the previously described manner.

It has been shown that the rehabilitating apparatus according to the present invention can be used by any injured leg regardless of its width and length and includes components that can be detached when the apparatus is not in use to facilitate packaging, storage and transport of the same.

While preferred embodiments have been illustrated and described, it will be apparent that many changes and modifications can be made in the general construction and arrangement of the present invention without departing from the scope and spirit thereof. Therefore, it is desired that the present invention be not limited to the exact disclosure but only to the extent of the appended claims.

I claim:

1. An apparatus for rehabilitating an injured leg, particularly a calf, comprising:
   an elongated rigid main support plate for supporting the calf, said main support plate having a top end, a bottom end, two opposed faces, a first engaging unit formed at said bottom end, and an opening formed adjacent to said first engaging unit;
   an elongated auxiliary cushioning plate;
   means for fastening said auxiliary cushioning plate detachably and removably along said top end of said main support plate and for permitting said auxiliary cushioning plate to extend beyond said top end in a longitudinal direction of said main support plate to vary a combined length of said main support plate and said auxiliary cushioning plate, wherein said fastening means include a row of aligned holes which are formed at said top end of said main support plate and which extend along said longitudinal length of said main support plate, a plurality of aligned slots which are formed adjacent to a lower end of said auxiliary cushioning plate and which extend along a longitudinal length of said auxiliary cushioning plate, and a plurality of screw fasteners;
   a rigid foot support plate conforming substantially to a foot and having a front end and a rear end with a second engaging unit which is engageable detachably with said first engaging unit of said main support plate to connect said foot support plate and said main support plate to form an L-shaped member; and
   means for securing the foot and the calf in position when the injured leg is provided on said L-shaped member, said securing means including a plurality of fastening straps.

2. The apparatus for rehabilitating an injured leg as defined in claim 1, wherein said first engaging unit includes a curved piece formed integrally at the bottom end of said main support plate, said curved piece having two opposed ends, an internal face and an external face, a pair of plug members being extending respectively from said opposed ends, and a curved insert piece integrally formed on said internal face of said curved piece, said second engaging unit including a recess formed at said rear end of said foot support plate and two opposed socket members located on two sides of said recess and capable of engaging said plug members when said insert piece is inserted into said recess.

3. The apparatus for rehabilitating an injured leg as defined in claim 1, wherein said first engaging unit includes a curved piece integrally formed at the bottom end of said main support plate, said curved piece having two opposed ends, an internal face, an external face, a pair of connecting stubs extending respectively from said opposed ends, and a curved insert piece integrally formed on said internal face of said curved piece, each of said connecting stubs having a mounting hole, said second engaging unit including a recess that is formed at said rear end of said foot support plate, a through-hole formed transversely through a longitudinal length of said foot support plate and located adjacent to said recess in alignment with said mounting holes of said connecting stubs, and a screw fastener which is capable of extending through said mounting holes and said through-hole, thereby preventing said main support plate from disengaging said foot support plate when said curved insert piece is inserted into said recess of said foot support plate.

4. The apparatus for rehabilitating an injured leg as defined in claim 1, wherein said first engaging unit includes a curved insert piece with two opposed connecting stubs, each of which having a mounting hole, said second engaging unit including a recess formed at said rear end of said foot support plate, two opposed threaded blind holes which are formed in said foot support plate adjacent to said recess, and a pair of screw fasteners which are capable of extending through said mounting holes in said connecting stubs so as to be threaded in said threaded blind bores, thereby preventing said main support plate from disengaging said foot support plate when said insert piece is inserted into said recess of said foot support plate.

5. The apparatus for rehabilitating an injured leg as defined in claim 1, wherein said foot support plate includes a first section, a second section and means for connecting said first and second sections to permit varying of a longitudinal length of said foot support plate, each of said first and second sections further having two opposed longitudinal peripheral edges, two opposed vertical positioning rods fixed symmetrically on each of said first and second sections along said longitudinal peripheral edges, and two L-shaped connecting members disposed on each of said first and second sections, each of said L-shaped connecting members including a first part contacting a respective one of said first and second sections and having an elongated first slot which extends transverse to said longitudinal length of said rigid foot support plate and which permits said vertical positioning rod to extend therethrough to prevent said L-shaped connecting member from disengaging a respective one of said first and second sections, and a second part which is substantially perpendicular to said first part, said second part having a second elongated slot that is parallel to said longitudinal length of said foot support plate, each said L-shaped connecting member being connected resiliently to another one of said L-shaped connecting members.

6. The apparatus for rehabilitating an injured leg as defined in claim 5, wherein said foot support plate further includes two cover members capable of covering threadedly a respective one of said first and second sections.

* * * * *